(12) United States Patent
Maeda et al.

(10) Patent No.: US 11,642,341 B2
(45) Date of Patent: May 9, 2023

(54) COMBINATION OF BREXPIPRAZOLE AND NALMEFENE AND USE THEREOF FOR TREATING SUBSTANCE-RELATED DISORDERS

(71) Applicants: OTSUKA PHARMACEUTICAL CO., LTD., Tokyo (JP); H. LUNDBECK A/S, Valby (DK)

(72) Inventors: Kenji Maeda, Osaka (JP); Mai Nakamura, Osaka (JP)

(73) Assignees: Otsuka Pharmaceutical Co., Ltd., Tokyo (JP); H. Lundbeck A/S, Valby (DK)

(*) Notice: Subject to any disclaimer, the term of this patent is extended or adjusted under 35 U.S.C. 154(b) by 0 days.

(21) Appl. No.: 16/992,551

(22) Filed: Aug. 13, 2020

(65) Prior Publication Data
US 2020/0368227 A1   Nov. 26, 2020

Related U.S. Application Data

(60) Division of application No. 16/250,548, filed on Jan. 17, 2019, now abandoned, which is a continuation of application No. 15/305,782, filed as application No. PCT/JP2015/062913 on Apr. 22, 2015, now abandoned.

(30) Foreign Application Priority Data

Apr. 22, 2014 (JP) ................................ 2014-088148

(51) Int. Cl.
A61K 31/496 (2006.01)
A61K 31/485 (2006.01)

(52) U.S. Cl.
CPC .......... *A61K 31/496* (2013.01); *A61K 31/485* (2013.01)

(58) Field of Classification Search
CPC ........ A61K 31/496; A61K 31/44; A61P 25/32
See application file for complete search history.

(56) References Cited

U.S. PATENT DOCUMENTS

| 5,086,058 | A  | * | 2/1992  | Sinclair  | A61P 25/32 514/282 |
| 7,888,362 | B2 | * | 2/2011  | Yamashita | A61P 25/00 514/253.05 |
| 2006/0235038 | A1 | * | 10/2006 | Simon     | A61K 31/485 514/282 |
| 2011/0152286 | A1 |   | 6/2011  | Yamashita | |
| 2015/0272946 | A1 | * | 10/2015 | Sato      | A61K 31/496 514/253.07 |

FOREIGN PATENT DOCUMENTS

| JP | 2003-514013 | 4/2003 |
| JP | 2008-512462 | 4/2008 |
| JP | 2008115172 | 5/2008 |
| JP | 2009-517393 | 4/2009 |
| RU | 2090190 | 9/1997 |
| WO | WO 91/18605 | 12/1991 |
| WO | WO 98/52565 | 11/1998 |
| WO | WO 01/35942 | 5/2001 |
| WO | WO 2005/089486 | 9/2005 |
| WO | WO-2005089486 A2 * | 9/2005 | ........... A61K 31/496 |
| WO | WO 2006/029167 | 3/2006 |
| WO | WO 2006/112464 | 10/2006 |
| WO | WO 2007/064586 | 6/2007 |
| WO | WO 2010/053835 | 5/2010 |
| WO | WO 2010/063292 | 6/2010 |
| WO | WO 2010/136039 | 12/2010 |
| WO | WO 2012/059103 | 5/2012 |
| WO | WO 2012/137971 | 10/2012 |
| WO | WO 2013/162046 | 10/2013 |
| WO | WO 2014/001427 | 1/2014 |
| WO | WO 2014/065437 | 5/2014 |
| WO | WO 2014/120936 | 8/2014 |

OTHER PUBLICATIONS

International Search Report for International Application No. PCT/JP2015/062913 dated Jul. 17, 2015 (6 pages).

Citrome L., "A Review of the Pharmacology, Efficacy and Toleravility of Recently Approved and Upcoming Oral Antiphychotics; An Evidence-Based Medicine Approach", CNS Drugs, vol. 27, pp. 879-911 (2013).

Written Opinion of the International Searching Authority or International Application No. PCT/JP2015/062913 dated Jul. 17, 2015 (6 pages).

Clinical Trials Gov. Safety and Efficacy of Nalmefene in Pateients with Alcohol Dependence (SENSE); Retrieved from https://clinicaltrials.gov/ct2/show/NCT00811941.

EMA. Nalmefene, Selincro; Retrived from http://www.ema.europa.eu/docs/en_GB/document_library/EPAR_-_Product_Information/human/002583/WC500140255.pdf.

(Continued)

*Primary Examiner* — Theodore R. Howell
*Assistant Examiner* — George W Kosturko
(74) *Attorney, Agent, or Firm* — Finnegan, Henderson, Farabow, Garrett & Dunner LLP

(57) ABSTRACT

A medicament comprising (I) brexpiprazole or a pharmaceutically acceptable salt thereof, and (II) nalmefene or a pharmaceutically acceptable salt thereof in combination, wherein brexpiprazole or a pharmaceutically acceptable salt thereof, and nalmefene or a pharmaceutically acceptable salt thereof are contained in a single preparation, or a pharmaceutical composition containing brexpiprazole or a pharmaceutically acceptable salt thereof and a pharmaceutical composition containing nalmefene or a pharmaceutically acceptable salt thereof are formulated for use in combination. The medicament is used for the prophylaxis or treatment of a substance-related disorder, preferably an alcohol-related disorder.

5 Claims, 1 Drawing Sheet

(56) References Cited

OTHER PUBLICATIONS

"Diagnostic and Statistical Manual of Mental Disorders, Fifth Edition, DSM-5", American Psychiatric Association, 2013, pp. 484, 485, 944.

DeLeon et al., "Aripiprazole: A Comprehensive Review of Its Pharmacology, Clinical Efficacy, and Tolerability," Clinical Therapeutics, 26(5):649-666 (2004).

Maeda, K. et al., "Brexpiprazole I: In Vitro and In Vivo Characterization of a Novel Seratonin-Dopamine Activity Modulator," J. Pharmacol Exp Ther. (2014); 350:589-604.

Mann, K. et al., "Extending the Treatment Options in Alcohol Dependence: A Randomized Controlled Study of As-Needed Nalmefene," Biol. Psychiatry (2013); 73:706-713.

Gual, A. et al., "A randomized, double-blind, placebo-controlled, efficacy study of nalmefene, as-needed use, in patients with alcohol dependence," European Neuropsychopharmacology (2013); 23(11):1432-1442.

Van den Brink, W. et al., "Long-term efficacy, tolerability and safety of nalmefene as-needed in patients with alcohol dependence: A 1-year, randomized controlled study," J. Psychpharm., 28(8):733-744 (2014) published on-line before print on Mar. 26, 2014.

Karhuvaara, S. et al., "Targeted Nalmefene With Simple Medical Management in the Treatment of Heavy Drinkers: A Randomized Double-Blind Placebo-Controlled Multicenter Study", Alcohol. Clin. Exp. Res. (2007); 31:1179-1187.

Voronin K E et al., Tolerability, Safety, and Efficacy of Aripiprazole and Naltrexone Combination in Non-treatment Seeking Alcoholics in a Natural Observation Paradigm, Alcoholism: Clinical and Experimental Research, Wiley-Blackwell Publishing, Inc., US, vol. 32, No. 6, Supplement 1, (2008) p. 255A.

Raymond, A. et al., "Naltrexone plus Aripiprazole compared to Naltrexone Alone and Placebo in the Treatment of Alcohol Dependence—A Double Blind Pilot Study," Neuropsychopharmacology, Elsevier Science Publishing, New York, NY, US., vol. 36, No. Supplement 1, (2011) pp. S234-S235.

Pettinati, Helen et al., A Double-Blind Placebo-Controlled Trial Containing Setraline and Naltrexone for Treating Co-Occurring Depression and Alcohol Dependence, American Journal of Psychiatry, Published online Jun. 1, 2010, 167(6):668-675, Washington DC.

Entsiklopedicheskiy slovar meditsinskikh terminov (Encyclopedic Dictionary of Medical Terms, ed. by V.I. Pokrovsky, $2^{nd}$ edition, Moscow, "Meditsina", 2001, p. 648.

Official Action issued in the corresponding Russian Patent Application No. 2016145411.

Maeda et al., "Brexpiprazole I: In Vitro and In Vivo Characterization of a Novel Serotonin-Dopamine Activity Modulator", *J. Pharmacol. Exp. Ther.*, 350: 589-604 (2014).

DeLeon et al., "Aripiprazole: A Comprehensive Review of It's Pharmacology, Clinical Efficacy, and Tolerability", *Clinical Therapeutics*, vol. 26, No. 5, pp. 649-666 (2004).

\* cited by examiner

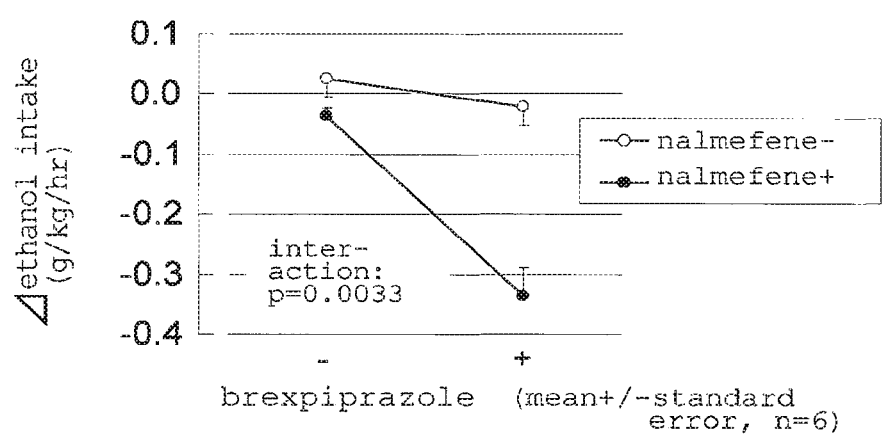

COMBINATION OF BREXPIPRAZOLE AND NALMEFENE AND USE THEREOF FOR TREATING SUBSTANCE-RELATED DISORDERS

This application is a Divisional of U.S. application Ser. No. 16/250,548, filed Jan. 17, 2019, which is a continuation of U.S. application Ser. No. 15/305,782, filed Oct. 21, 2016, which is a national phase application based on PCT/JP2015/062913, filed Apr. 22, 2015, which claims the benefit of Japanese Application No. 2014-088148, filed Apr. 22, 2014, the contents of all of which are incorporated herein by reference in their entireties.

TECHNICAL FIELD

The present invention relates to a medicament using brexpiprazole or a pharmaceutically acceptable salt thereof and nalmefene or a pharmaceutically acceptable salt thereof in combination.

BACKGROUND ART

It is known that brexpiprazole (7-[4-(4-benzo[b]thiophen-4-yl-piperazin-1-yl)butoxy]-1H-quinolin-2-one) or a pharmaceutically acceptable salt thereof has a dopamine $D_2$ receptor partial agonist activity ($D_2$ receptor partial agonist activity), a serotonin 5-$HT_{2A}$ receptor antagonist activity (5-$HT_{2A}$ receptor antagonist activity) and an adrenergic $\alpha_1$ receptor antagonist activity ($\alpha_1$ receptor antagonist activity) and, in addition thereto, concurrently has a serotonin uptake inhibitory action (or serotonin reuptake inhibitory action) (patent document 1 and patent document 2). In addition, it is known that brexpiprazole has a serotonin 5-$HT_{1A}$ receptor antagonist activity (5-$HT_{1A}$ receptor antagonist activity) (non-patent document 1).

Nalmefene (17-(cyclopropylmethyl)-4,5α-epoxy-6-methylenemorphinan-3,14-diol) has the following formula

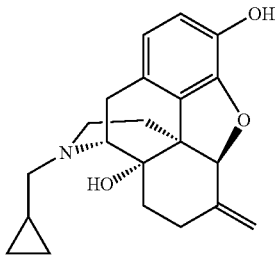 [SMILES: C=C1CC[C@@]2(O)[C@H]3Cc4ccc(O)c5c4[C@@]2(CCN3CC2CC2)[C@H]1O5]

and can be prepared using methods that are well known in the art e.g. starting by manufacturing of naltrexone from noroxymorphone as described in WO2012/059103 (patent document 3) and subsequently manufacturing nalmefene from naltrexone e.g. by the Wittig reactin as described in WO2010/136039 (patent document 4).

Nalmefene is an opioid system modulator with a distinct µ, δ and κ receptor profile. In vitro studies have demonstrated that nalmefene is a selective opioid receptor ligand with antagonist activity at the µ and δ receptors and partial agonist activity at the κ receptor. Acute alcohol intake was shown to result in mesolimbic dopamine release (facilitated by the release of β-endorphins), which can provide positive reinforcement. Nalmefene is thought to counteract the reinforcement effects and to reduce alcohol consumption, possibly by modulating these cortico-mesolimbic functions.

The efficacy and tolerability of nalmefene in the treatment of alcohol dependence have been evaluated in three phase III studies (two confirmatory 6-month efficacy studies and one 1-year safety study) conducted by Lundbeck (non-patent documents 2 to 4) and 5 studies in alcohol use disorders conducted by the company Biotie (non-patent document 5).

In February 2013, a marketing authorization has been granted for oral nalmefene in the European Union (EU) under the tradename Selincro (registered trademark) for the reduction of alcohol consumption in adult patients with alcohol dependence.

WO2005/089486 (patent document 5) discloses that when coadministered with an opioid antagonist naltrexone, a dopamine $D_2$ receptor partial agonist aripiprazole does not affect (i.e., neither impairs nor enhances) naltrexone's ability to decrease ethanol intake.

DOCUMENT LIST

Patent Documents patent document 1: WO2006/112464
patent document 2: JP-A-2008-115172
patent document 3: WO2012/059103
patent document 4: WO2010/136039
patent document 5: WO2005/089486

Non-Patent Documents non-patent document 1: Maeda et al., Brexpiprazole I: In Vitro and In Vivo Characterization of a Novel Serotonin-Dopamine Activity Modulator. J Pharmacol Exp Ther (2014); 350:589-604
non-patent document 2: Mann et al., Extending the Treatment Options in Alcohol Dependence: A Randomized Controlled Study of As-Needed Nalmefene. Biol. Psychiatry (2013); 73: 706-713
non-patent document 3: Gual et al., A randomised, double-blind, placebo-controlled, efficacy study of nalmefene, as-needed use, in patients with alcohol dependence. European Neuropsychopharmacology (2013); 23(11): 1432-1442
non-patent document 4: van den Brink et al., Long-term efficacy, tolerability and safety of nalmefene as-needed in patients with alcohol dependence: A 1-year, randomised controlled study. J. Psychopharmacol., published online before print Mar. 26, 2014, doi: 10.1177/0269881114527362
non-patent document 5: Karhuvaara et al., Alcohol. Clin. Exp. Res. (2007); 31: 1179-1187

SUMMARY OF THE INVENTION

Problems to be Solved by the Invention

The object of the present invention is to provide a medicament for use in the prophylaxis or treatment of substance-related disorders such as alcohol-related disorder and the like.

Means of Solving the Problems

As mentioned above, a combined administration of naltrexone which is an opioid antagonist and aripiprazole which is a dopamine $D_2$ receptor partial agonist does not affect the ability of both drugs. That is, it is disclosed that such combined administration does not show a synergistic effect or even an additive effect. In such situation, the present inventors have conducted intensive studies in an attempt to solve the aforementioned problems and found that the use of nalmefene which is an opioid antagonist and brexpiprazole which is a dopamine $D_2$ receptor partial agonist in combination surprisingly affords not only an additive effect but also a synergistic effect. The present invention has been completed based on such finding.

The present invention preferably provides medicaments, use, methods for preventing or treating diseases, a pharmaceutical composition, a production method of a pharmaceutical composition and kits shown in item 1 to item 63 below.

Item 1.

A medicament comprising (I) brexpiprazole or a pharmaceutically acceptable salt thereof, and (II) nalmefene or a pharmaceutically acceptable salt thereof in combination, wherein brexpiprazole or a pharmaceutically acceptable salt thereof, and nalmefene or a pharmaceutically acceptable salt thereof are contained in a single preparation, or a pharmaceutical composition containing brexpiprazole or a pharmaceutically acceptable salt thereof and a pharmaceutical composition containing nalmefene or a pharmaceutically acceptable salt thereof are formulated for use in combination.

Item 2.

The medicament according to item 1, wherein (I) brexpiprazole or a pharmaceutically acceptable salt thereof, and (II) nalmefene or a pharmaceutically acceptable salt thereof are contained in a single preparation.

Item 3.

The medicament according to item 1, wherein a pharmaceutical composition containing brexpiprazole or a pharmaceutically acceptable salt thereof and a pharmaceutical composition containing nalmefene or a pharmaceutically acceptable salt thereof are formulated for use in combination.

Item 4.

The medicament according to any one of items 1 to 3, for use in the prophylaxis or treatment of a substance-related disorder.

Item 5.

The medicament according to item 4, wherein the substance-related disorder is an alcohol-related disorder.

Item 6.

The medicament according to item 5, wherein the alcohol-related disorder is selected from the group consisting of an alcohol use disorder, an alcohol-induced disorder, alcohol abuse, alcohol dependence, alcohol intoxication and an alcohol withdrawal symptom.

Item 7.

The medicament according to item 5, for use in the prophylaxis or treatment of an impulsive symptom in an alcohol-related disorder.

Item 8.

The medicament according to item 7, wherein the alcohol-related disorder is selected from the group consisting of an alcohol use disorder, an alcohol-induced disorder, alcohol abuse, alcohol dependence, alcohol intoxication and an alcohol withdrawal symptom.

Item 9.

The medicament according to item 8, wherein the alcohol-related disorder is alcohol dependence.

Item 10.

A medicament comprising brexpiprazole or a pharmaceutically acceptable salt thereof, for a combined use with nalmefene or a pharmaceutically acceptable salt thereof.

Item 11.

A medicament comprising nalmefene or a pharmaceutically acceptable salt thereof, for a combined use with brexpiprazole or a pharmaceutically acceptable salt thereof.

Item 12.

Use of (I) brexpiprazole or a pharmaceutically acceptable salt thereof in combination with (II) nalmefene or a pharmaceutically acceptable salt thereof for the production of a medicament for the prophylaxis or treatment of a substance-related disorder.

Item 13.

Use according to item 12, wherein the substance-related disorder is an alcohol-related disorder.

Item 14.

Use according to item 13, wherein the alcohol-related disorder is selected from the group consisting of an alcohol use disorder, an alcohol-induced disorder, alcohol abuse, alcohol dependence, alcohol intoxication and an alcohol withdrawal symptom.

Item 15.

Use according to item 13, wherein the medicament is for use in the prophylaxis or treatment of an impulsive symptom in an alcohol-related disorder.

Item 16.

Use according to item 15, wherein the alcohol-related disorder is selected from the group consisting of an alcohol use disorder, an alcohol-induced disorder, alcohol abuse, alcohol dependence, alcohol intoxication and an alcohol withdrawal symptom.

Item 17.

Use according to item 16, wherein the alcohol-related disorder is alcohol dependence.

Item 18.

A method for preventing or treating a substance-related disorder, comprising administering (I) brexpiprazole or a pharmaceutically acceptable salt thereof, and (II) nalmefene or a pharmaceutically acceptable salt thereof to a subject in need thereof, wherein brexpiprazole or a pharmaceutically acceptable salt thereof, and nalmefene or a pharmaceutically acceptable salt thereof are administered as a single preparation or separate preparations simultaneously or separately in a staggered manner.

Item 19.

The method according to item 18, wherein the substance-related disorder is an alcohol-related disorder.

Item 20.

The method according to item 19, wherein the alcohol-related disorder is selected from the group consisting of an alcohol use disorder, an alcohol-induced disorder, alcohol abuse, alcohol dependence, alcohol intoxication and an alcohol withdrawal symptom.

Item 21.

The method according to item 19, which is a method for preventing or treating an impulsive symptom in an alcohol-related disorder.

Item 22.

The method according to item 21, wherein the alcohol-related disorder is selected from the group consisting of an alcohol use disorder, an alcohol-induced disorder, alcohol abuse, alcohol dependence, alcohol intoxication and an alcohol withdrawal symptom.

Item 23.

The method according to item 22, wherein the alcohol-related disorder is alcohol dependence.

Item 24.

A pharmaceutical composition comprising (I) brexpiprazole or a pharmaceutically acceptable salt thereof, (II)

nalmefene or a pharmaceutically acceptable salt thereof, and (III) a pharmacologically acceptable carrier.

Item 25.

A method for producing a pharmaceutical composition, comprising mixing (I) brexpiprazole or a pharmaceutically acceptable salt thereof and (II) nalmefene or a pharmaceutically acceptable salt thereof with a pharmacologically acceptable carrier.

Item 26.

A kit comprising (I) a medicament containing brexpiprazole or a pharmaceutically acceptable salt thereof, and (II) a medicament containing nalmefene or a pharmaceutically acceptable salt thereof.

Item 27.

The kit according to item 26, for use in the prophylaxis or treatment of a substance-related disorder.

Item 28.

The kit according to item 27, wherein the substance-related disorder is an alcohol-related disorder.

Item 29.

The medicament according to any one of items 1 to 11, wherein brexpiprazole or a pharmaceutically acceptable salt thereof is a solvate of brexpiprazole or of a pharmaceutically acceptable salt thereof.

Item 30.

The medicament according to item 29, wherein the solvate is dihydrate.

Item 31.

The medicament according to any one of items 1 to 11, 29 and 30, wherein nalmefene or a pharmaceutically acceptable salt thereof is monohydrate or dihydrate of nalmefene or of a pharmaceutically acceptable salt thereof.

Item 32.

The medicament according to item 31, wherein nalmefene or a pharmaceutically acceptable salt thereof is dihydrate of nalmefene or of a pharmaceutically acceptable salt thereof.

Item 33.

The medicament according to item 32, wherein nalmefene or a pharmaceutically acceptable salt thereof is nalmefene hydrochloride dihydrate.

Item 34.

Use according to any one of items 12 to 17, wherein brexpiprazole or a pharmaceutically acceptable salt thereof is a solvate of brexpiprazole or of a pharmaceutically acceptable salt thereof.

Item 35.

Use according to item 34, wherein the solvate is dihydrate.

Item 36.

Use according to any one of items 12 to 17, 34 and 35, wherein nalmefene or a pharmaceutically acceptable salt thereof is monohydrate or dihydrate of nalmefene or of a pharmaceutically acceptable salt thereof.

Item 37.

Use according to item 36, wherein nalmefene or a pharmaceutically acceptable salt thereof is dihydrate of nalmefene or of a pharmaceutically acceptable salt thereof.

Item 38.

Use according to item 37, wherein nalmefene or a pharmaceutically acceptable salt thereof is nalmefene hydrochloride dihydrate.

Item 39.

The method according to any one of items 18 to 23, wherein brexpiprazole or a pharmaceutically acceptable salt thereof is a solvate of brexpiprazole or of a pharmaceutically acceptable salt thereof.

Item 40.

The method according to item 39, wherein the solvate is dihydrate.

Item 41.

The method according to any one of items 18 to 23, 39 and 40, wherein nalmefene or a pharmaceutically acceptable salt thereof is monohydrate or dihydrate of nalmefene or of a pharmaceutically acceptable salt thereof.

Item 42.

The method according to item 41, wherein nalmefene or a pharmaceutically acceptable salt thereof is dihydrate of nalmefene or of a pharmaceutically acceptable salt thereof.

Item 43.

The method according to item 42, wherein nalmefene or a pharmaceutically acceptable salt thereof is nalmefene hydrochloride dihydrate.

Item 44.

The pharmaceutical composition according to item 24, wherein brexpiprazole or a pharmaceutically acceptable salt thereof is a solvate of brexpiprazole or of a pharmaceutically acceptable salt thereof.

Item 45.

The pharmaceutical composition according to item 44, wherein the solvate is dihydrate.

Item 46.

The pharmaceutical composition according to any one of items 24, 44 and 45, wherein nalmefene or a pharmaceutically acceptable salt thereof is monohydrate or dihydrate of nalmefene or of a pharmaceutically acceptable salt thereof.

Item 47.

The pharmaceutical composition according to item 46, wherein nalmefene or a pharmaceutically acceptable salt thereof is dihydrate of nalmefene or of a pharmaceutically acceptable salt thereof.

Item 48.

The pharmaceutical composition according to item 47, wherein nalmefene or a pharmaceutically acceptable salt thereof is nalmefene hydrochloride dihydrate.

Item 49.

The kit according to any one of items 26 to 28, wherein brexpiprazole or a pharmaceutically acceptable salt thereof is a solvate of brexpiprazole or of a pharmaceutically acceptable salt thereof.

Item 50.

The kit according to item 49, wherein the solvate is dihydrate.

Item 51.

The kit according to any one of items 26 to 28, 49 and 50, wherein nalmefene or a pharmaceutically acceptable salt thereof is monohydrate or dihydrate of nalmefene or of a pharmaceutically acceptable salt thereof.

Item 52.

The kit according to item 51, wherein nalmefene or a pharmaceutically acceptable salt thereof is dihydrate of nalmefene or of a pharmaceutically acceptable salt thereof.

Item 53.

The kit according to item 52, wherein nalmefene or a pharmaceutically acceptable salt thereof is nalmefene hydrochloride dihydrate.

Item 54.

The medicament according to any one of items 1 to 3, for treating a patient for whom an existing therapeutic drug for alcohol-related disorder provides only an insufficient effect.

Item 55.

The medicament according to item 54, wherein the existing therapeutic drug for alcohol-related disorder is selected from the group consisting of cyanamide, disulfiram, acamprosate, nalmefene and naltrexone.

Item 56.

A medicament for use in the treatment of an alcohol-related disorder, comprising brexpiprazole or a pharmaceutically acceptable salt thereof as an active ingredient, which is used for a patient receiving a treatment with a preparation of nalmefene or a pharmaceutically acceptable salt thereof.

Item 57.

A medicament for use in the treatment of an alcohol-related disorder, comprising nalmefene or a pharmaceutically acceptable salt thereof as an active ingredient, which is used for a patient receiving a treatment with a preparation of brexpiprazole or a pharmaceutically acceptable salt thereof.

Item 58.

The medicament according to item 6, wherein brexpiprazole or a pharmaceutically acceptable salt thereof is brexpiprazole, and nalmefene or a pharmaceutically acceptable salt thereof is nalmefene hydrochloride dihydrate.

Item 59.

The medicament according to item 8, wherein brexpiprazole or a pharmaceutically acceptable salt thereof is brexpiprazole, and nalmefene or a pharmaceutically acceptable salt thereof is nalmefene hydrochloride dihydrate.

Item 60.

Use according to item 14, wherein brexpiprazole or a pharmaceutically acceptable salt thereof is brexpiprazole, and nalmefene or a pharmaceutically acceptable salt thereof is nalmefene hydrochloride dihydrate.

Item 61.

Use according to item 16, wherein brexpiprazole or a pharmaceutically acceptable salt thereof is brexpiprazole, and nalmefene or a pharmaceutically acceptable salt thereof is nalmefene hydrochloride dihydrate.

Item 62.

The method according to item 20, wherein brexpiprazole or a pharmaceutically acceptable salt thereof is brexpiprazole, and nalmefene or a pharmaceutically acceptable salt thereof is nalmefene hydrochloride dihydrate.

Item 63.

The method according to item 22, wherein brexpiprazole or a pharmaceutically acceptable salt thereof is brexpiprazole, and nalmefene or a pharmaceutically acceptable salt thereof is nalmefene hydrochloride dihydrate.

Item 64.

The pharmaceutical composition according to item 24, wherein brexpiprazole or a pharmaceutically acceptable salt thereof is brexpiprazole, and nalmefene or a pharmaceutically acceptable salt thereof is nalmefene hydrochloride dihydrate.

Item 65.

The method for producing a pharmaceutical composition according to item 25, wherein brexpiprazole or a pharmaceutically acceptable salt thereof is brexpiprazole, and nalmefene or a pharmaceutically acceptable salt thereof is nalmefene hydrochloride dihydrate.

Item 66.

The kit according to item 28, wherein brexpiprazole or a pharmaceutically acceptable salt thereof is brexpiprazole, and nalmefene or a pharmaceutically acceptable salt thereof is nalmefene hydrochloride dihydrate.

Effect of the Invention

A combined administration of brexpiprazole and nalmefene can afford a synergistic effect as compared to single administration of each medicament. A combined use of extremely low doses of brexpiprazole and nalmefene can suppress an impulsive ethanol-intake behavior. In addition, the combined use of the both medicaments is shown to enable brexpiprazole to enhance the treatment effect of nalmefene. In addition, the combined use of the both medicaments is shown to enable nalmefene to enhance the treatment effect of brexpiprazole. Lower side effects are expected as a result of the lower doses that may be applied.

BRIEF DESCRIPTION OF THE DRAWING

FIG. 1 is a graph showing the test results of Example 1.

DESCRIPTION OF EMBODIMENTS

Preferable examples of the pharmaceutically acceptable salt of brexpiprazole usable in the present invention include salt with inorganic acid such as sulfate, nitrate, hydrochloride, phosphate, hydrobromide and the like; salt with organic acid such as acetate, sulfonate (e.g., p-toluenesulfonate, methanesulfonate, ethanesulfonate etc.), oxalate, maleate, fumarate, malate, tartrate, citrate, succinate, pamoate, benzoate and the like. Brexpiprazole or a pharmaceutically acceptable salt thereof may be a solvate. The preferred example of the solvate is dihydrate of brexpiprazole or of a pharmaceutically acceptable salt thereof (WO2013/162046).

Brexpiprazole or a pharmaceutically acceptable salt thereof usable in the present invention is also encompasses the same isotopically-labeled compounds, wherein one or plural atoms is(are) replaced by one or plural atoms having a particular atomic mass or mass number. Examples of the isotope that can be incorporated into brexpiprazole or a pharmaceutically acceptable salt thereof include hydrogen, carbon, nitrogen, oxygen, sulfur, fluorine and chlorine isotopes such as $^2H$, $^3H$, $^{13}C$, $^{14}C$, $^{15}N$, $^{18}O$, $^{17}O$, $^8F$, $^{36}Cl$ and the like. Certain isotopically-labeled brexpiprazole or a pharmaceutically acceptable salt thereof, which contains the above-mentioned isotope and/or other isotope of other atom, for example, brexpiprazole or a pharmaceutically acceptable salt thereof incorporating a radioactive isotope such as $^3H$, $^{14}C$ and the like, is useful for drug tissue distribution assay and/or substrate tissue distribution assay. Tritiated (i.e., $^3H$) or carbon-14 (i.e., $^{14}C$) isotope are particularly preferred because of easiness of preparation and detectability. Furthermore, substitution with a heavier isotope such as deuterium (i.e., $^2H$) and the like is expected to provide improved metabolic stability and particular therapeutic advantage attributable to increased in vivo half-life or decreased amount necessary for administration. An isotopically-labeled compound of brexpiprazole or a pharmaceutically acceptable salt thereof can be generally prepared according to the method disclosed in WO2006/112464 and WO2013/162046, by substituting a non-isotopically-labeled reagent with an easily available isotopically-labeled reagent.

Brexpiprazole or a pharmaceutically acceptable salt thereof, a production method thereof, a dose to be used thereof and the like are disclosed in WO2006/112464 and WO2013/162046, and the disclosure thereof is incorporated herein by reference.

Nalmefene or a pharmaceutically acceptable salt thereof, a production method thereof, a dose to be used thereof and the like are disclosed in U.S. Pat. Nos. 3,814,768, 4,751,307, 4,535,157 and WO2010/063292, and the disclosure thereof is incorporated herein by reference.

Examples of the pharmaceutically acceptable salt of nalmefene include hydrochloride, hydrochloride monohydrate, hydrochloride dihydrate and the like. A more preferable example is nalmefene hydrochloride dihydrate.

A medicament using brexpiprazole or a pharmaceutically acceptable salt thereof in combination with nalmefene or a pharmaceutically acceptable salt thereof has an excellent effect. Therefore, such medicament is expected to cause a fewer side effects and has an excellent safety profile as a results of lower doses that may be applied.

Brexpiprazole or a pharmaceutically acceptable salt thereof and nalmefene or a pharmaceutically acceptable salt thereof may be administered orally or parenterally.

In the present specification, when a medicament comprising brexpiprazole or a pharmaceutically acceptable salt thereof in combination with nalmefene or a pharmaceutically acceptable salt thereof is used, the administration period of brexpiprazole or a pharmaceutically acceptable salt thereof and nalmefene or a pharmaceutically acceptable salt thereof is not limited, and brexpiprazole or a pharmaceutically acceptable salt thereof and nalmefene or a pharmaceutically acceptable salt thereof may be simultaneously formulated into a single preparation, or brexpiprazole or a pharmaceutically acceptable salt thereof or a pharmaceutical composition thereof and nalmefene or a pharmaceutically acceptable salt thereof or a pharmaceutical composition thereof may be administered to a subject of administration simultaneously or in a staggered manner. When brexpiprazole or a pharmaceutically acceptable salt thereof and nalmefene or a pharmaceutically acceptable salt thereof are administered, they may be administered simultaneously. Alternatively, nalmefene or a pharmaceutically acceptable salt thereof may be administered in advance, and then brexpiprazole or a pharmaceutically acceptable salt thereof may be administered, or brexpiprazole or a pharmaceutically acceptable salt thereof may be administered in advance, and then nalmefene or a pharmaceutically acceptable salt thereof may be administered. For administration in a staggered manner, the time difference varies depending on the dosage form and administration method. For example, when brexpiprazole or a pharmaceutically acceptable salt thereof is to be administered in advance, a method including administering nalmefene or a pharmaceutically acceptable salt thereof within 1 min-3 days, preferably 10 min-1 day, more preferably 15 min-1 hr, after the administration of brexpiprazole or a pharmaceutically acceptable salt thereof can be mentioned. The dose of nalmefene or a pharmaceutically acceptable salt thereof may be similar to the dose clinically used, and can be appropriately determined according to the subject of administration, administration route, disease and the like.

The administration form of the medicament of the present invention is not particularly limited, and brexpiprazole or a pharmaceutically acceptable salt thereof and nalmefene or a pharmaceutically acceptable salt thereof only need to be combined on administration. Examples of such administration form include (1) administration of a single preparation obtained by simultaneously formulating brexpiprazole or a pharmaceutically acceptable salt thereof and nalmefene or a pharmaceutically acceptable salt thereof, (2) simultaneous administration of two kinds of preparations obtained by separately formulating brexpiprazole or a pharmaceutically acceptable salt thereof and nalmefene or a pharmaceutically acceptable salt thereof by the same administration route, (3) administration of two kinds of preparations obtained by separately formulating brexpiprazole or a pharmaceutically acceptable salt thereof and nalmefene or a pharmaceutically acceptable salt thereof by the same administration route in a staggered manner (e.g., administration in the order of brexpiprazole or a pharmaceutically acceptable salt thereof; nalmefene or a pharmaceutically acceptable salt thereof, or administration in the reverse order), (4) simultaneous administration of two kinds of preparations obtained by separately formulating brexpiprazole or a pharmaceutically acceptable salt thereof and nalmefene or a pharmaceutically acceptable salt thereof by different administration routes, (5) administration of one or more kinds of preparations obtained by separately formulating brexpiprazole or a pharmaceutically acceptable salt thereof and nalmefene or a pharmaceutically acceptable salt thereof by different administration routes in a staggered manner (e.g., administration in the order of brexpiprazole or a pharmaceutically acceptable salt thereof; nalmefene or a pharmaceutically acceptable salt thereof, or in the reverse order) and the like.

The medicaments of the present invention comprising brexpiprazole or a pharmaceutically acceptable salt thereof, nalmefene or a pharmaceutically acceptable salt thereof and/or brexpiprazole or a pharmaceutically acceptable salt thereof and nalmefene or a pharmaceutically acceptable salt thereof in combination, which are constituent components of the present invention, show low toxicity and, for example, brexpiprazole or a pharmaceutically acceptable salt thereof and/or nalmefene or a pharmaceutically acceptable salt thereof can be mixed with a pharmacologically acceptable carrier according to a known method to give a pharmaceutical composition, such as tablets (including sugar-coated tablet, film-coated tablet), powders, granules, capsules (including soft capsule), liquids, injections, suppositories, sustained-release preparations and the like, which can be safely administered orally or parenterally (e.g., local, rectum, vein, and the like). An injection can be administered by intravenous, intramuscular, subcutaneous or intraorgan administration or directly to the lesion. As a pharmacologically acceptable carrier which may be used for producing the pharmaceutical composition of the present invention, excipient, disintegrant, binder, glidant, lubricant, coating agent, colorant, suspending agent, sweetening agent or surfactant is appropriately used, and a general pharmaceutical preparation is formed according to a known method. Examples of the form of the pharmaceutical preparation include powder, tablet, pill, capsule and the like.

Examples of the excipient include lactose, anhydrous lactose, purified sucrose, sucrose, D-mannitol, D-sorbitol, xylitol, erythritol, dextrin, crystalline cellulose, microcrystalline cellulose, cornstarch, potato starch, anhydrous calcium hydrogen phosphate and the like.

Examples of the disintegrant include sodium carboxymethyl starch, carmellose, carmellose calcium, carmellose sodium, croscarmellose sodium, crospovidone, low-substituted hydroxypropylcellulose, partially pregelatinized starch and the like.

Examples of the binder include hydroxypropylcellulose, hydroxypropylmethylcellulose, polyvinylpyrrolidone, pregelatinized starch, syrup, starch syrup and the like.

Examples of the glidant include light anhydrous silicic acid, synthetic aluminum silicate, hydrated silicon dioxide, calcium stearate, magnesium aluminometasilicate, talc and the like.

Examples of the lubricant include magnesium stearate, calcium stearate, magnesium silicate, magnesium oxide, talc, hydrogenated oil, sucrose fatty acid ester, sodium stearyl fumarate and the like.

Examples of the coating agent include hydroxypropylmethylcellulose, polyvinyl alcohol, polysorbate, macrogol, talc and the like.

Examples of the colorant include yellow iron sesquioxide, brown iron oxide, iron sesquioxide, black iron oxide, titanium oxide, Food Blue No. 1, Food Red No. 2, Food Red No. 3, Food Yellow No. 4 and the like.

Examples of the suspending agent include polysorbate, polyethylene glycol, gum arabic, glycerol, gelatin and the like.

Examples of the sweetening agent include aspartame, saccharin, saccharin sodium, starch syrup, fructose and the like.

Examples of the surfactant include sodium lauryl sulfate, polysorbate, polyoxyethylene hydrogenated castor oil and the like.

A capsule is prepared by filling a hard capsule such as gelatin capsule, hydroxypropylmethylcellulose capsule, polyvinyl alcohol capsule and the like or a soft capsule based on gelatin, according to a known method. Conventional various organic or inorganic carrier substances can be used as preparation starting materials and examples thereof include excipient, lubricant, binder and disintegrant for solid preparations, and solvent, solubilizing agent, suspending agent, isotonic agent, buffering agent and soothing agent for liquid preparations and the like. Furthermore, where necessary, additives such as general preservative, antioxidant, colorant, sweetening agent, adsorbent, wetting agent and the like can be appropriately used in an appropriate amount.

Dose

The dose of brexpiprazole or a pharmaceutically acceptable salt thereof and nalmefene or a pharmaceutically acceptable salt thereof to be used in the present invention is determined in consideration of the properties of the drug after combination, and the condition of the patients. As shown above, brexpiprazole or a pharmaceutically acceptable salt thereof and nalmefene or a pharmaceutically acceptable salt thereof may be separately administered without being combined in one composition. As the general outline of the dose, for example, the following guideline can be applied.

In the following description of the dose, for example, "about 0.005-about 50 mg/2 times/1 day" means administration of about 0.005-about 50 mg per administration twice a day.

Brexpiprazole or a pharmaceutically acceptable salt thereof: generally about 0.01-about 100 mg/1 time/1 day (or about 0.005-about 50 mg/2 times/1 day), preferably about 0.1-about 4 mg/1 time/1 day (or about 0.05-about 2 mg/2 times/i day). The dose may be 0.05-2 mg/1 time/1 day on an as-needed basis.

Nalmefene or a pharmaceutically acceptable salt thereof: generally about 0.1-about 100 mg/1 time/1 day (or about 0.05-about 50 mg/2 times/1 day), preferably about 1-about 20 mg/1 time/1 day (or about 0.5-about 10 mg/2 times/1 day). The dose may be 0.5-10 mg/1 time/1 day on an as-needed basis.

In the present invention, the proportion of brexpiprazole or a pharmaceutically acceptable salt thereof and nalmefene or a pharmaceutically acceptable salt thereof to be used may be generally about 0.01-about 500 parts by weight, preferably about 0.1-about 100 parts by weight, of the latter relative to 1 part by weight of the former.

The mixing ratio of brexpiprazole or a pharmaceutically acceptable salt thereof and nalmefene or a pharmaceutically acceptable salt thereof in the medicament of the present invention can be appropriately determined according to the subject of administration, administration route, disease and the like. For example, while the total proportion of brexpiprazole or a pharmaceutically acceptable salt thereof and nalmefene or a pharmaceutically acceptable salt thereof in the medicament of the present invention varies depending on the preparation form, it is generally about 0.01-about 99.99 wt %, preferably about 0.1-about 99.9 wt %, more preferably about 1-about 30 wt %, relative to the whole preparation. The above-mentioned pharmacologically acceptable carrier is used for the remaining part.

In addition, when brexpiprazole or a pharmaceutically acceptable salt thereof and nalmefene or a pharmaceutically acceptable salt thereof are to be separately formulated, a similar content may be used.

The present invention may also be in the form of a kit comprising a medicament containing brexpiprazole or a pharmaceutically acceptable salt thereof and a medicament containing nalmefene or a pharmaceutically acceptable salt thereof, which are separately formulated. The kind of the preparation is not particularly limited, and tablets (including sugar-coated tablet, film-coated tablet), powder, granule, capsule (including soft capsule), liquid, injection, suppository, sustained-release preparation and the like can be mentioned. Preferred is, for example, a kit comprising an oral preparation containing brexpiprazole or a pharmaceutically acceptable salt thereof (tablet, powder, granule, capsule or liquid), and an oral preparation containing nalmefene or a pharmaceutically acceptable salt thereof (tablet, powder, granule, capsule or liquid).

The medicament and pharmaceutical composition of the present invention are useful for the prophylaxis or treatment of substance-related disorders (e.g., alcohol-related disorder (alcohol use disorder, alcohol-induced disorder, alcohol abuse, alcohol dependence, alcohol intoxication, alcohol withdrawal symptoms, etc.), amphetamine-related disorder (amphetamine use disorder etc.), *Cannabis*-related disorder (*Cannabis* use disorder etc.), cocaine-related disorder (cocaine use disorder etc.), hallucinogen-related disorder (hallucinogen use disorder etc.) and the like).

In addition, the medicament and pharmaceutical composition of the present invention are useful for the prophylaxis or treatment of an impulsive symptom in substance-related disorders (e.g., alcohol-related disorder (alcohol use disorder, alcohol-induced disorder, alcohol abuse, alcohol dependence, alcohol intoxication, alcohol withdrawal symptoms, etc.), amphetamine-related disorder (amphetamine use disorder etc.), *Cannabis*-related disorder (*Cannabis* use disorder etc.), cocaine-related disorder (cocaine use disorder etc.), hallucinogen-related disorder (hallucinogen use disorder etc.) and the like).

The medicament and pharmaceutical composition of the present invention are particularly useful for the prophylaxis or treatment of alcohol-related disorders, and the prophylaxis or treatment of an impulsive symptom in alcohol-related disorders.

The impulsive symptom is a symptom associated with an impulsive action. Specific examples of the impulsive behavior include physical attack, wandering, restlessness, agitation, senseless behavior and deviant behavior (e.g., sexual deviant behavior), roaming, shrill voice, screaming, violent language, loss of motivation, constant questioning, shadowing, suicide attempt and suicide, self-injurious behavior, threat, stealing, overeating, act of threatening, short-circuit reaction, panic reaction, property damage, inappropriate dressing/undressing, underselling and the like. Specific examples of the impulsive symptom in alcohol-related disorders include not only impulsive drinking behavior wherein a patient cannot suppress an intake action of alcohol, but also a symptom to take quick action to satisfy the immediate desire even though it can lead to an undesirable effect in the future. In the latter case, patients often commit a crime such as violent behavior and the like.

The medicament and pharmaceutical composition of the present invention can be used for treating a patient for whom an existing therapeutic drug for alcohol-related disorder provides only an insufficient effect.

The "patient for whom an existing therapeutic drug for alcohol-related disorder provides only an insufficient effect" means "those who could not achieve a Medium risk (male: 41 to 60 g/day, female: 21 to 40 g/day) or below in a sobriety treatment according to the standard of WHO drinking classification (WHO/MSD/MSB/00.4, INTERNATIONAL GUIDE FOR MONITORING ALCOHOL CONSUMPTION AND RELATED HARM, chapter 2.2 and The quantification of drug-caused mortality and morbidity in Australia, 1998, chapter 2.5.1), or those who could not achieve abstinence from alcohol by an alcohol abstinence therapy".

Examples of the existing therapeutic drugs for alcohol-related disorder includes (1) antialcoholic drugs (cyanamide, disulfiram, etc.),
(2) therapeutic drugs for alcohol dependence (acamprosate etc.),
(3) drugs for reducing alcohol consumption (nalmefene, naltrexone etc.),
(4) antipsychotics (atypical antipsychotics such as aripiprazole, quetiapine, olanzapine, risperidone, etc. and typical antipsychotics),
(5) antiepileptic agents (topiramate, zonisamide, gabapentin, vigabatrin, lamotrigine, valproic acid, carbamazepine, etc.),
(6) antidepressants [selective serotonin reuptake inhibitors (fluoxetine, citalopram, fluvoxamine, paroxetine, sertraline, escitalopram, etc.), serotonin and norepinephrine reuptake inhibitors (venlafaxine, duloxetine, milnacipran, desvenlafaxine, etc.), noradrenergic and specific serotonergic antidepressants (mirtazapine etc.), tricyclic and tetracyclic antidepressants (desipramine etc.), monoamine oxidase inhibitors, etc.],
(7) antianxiety drugs or sleeping drugs (ethyl loflazepate, etizolam, nitrazepam, flunitrazepam, zopiclone, mianserin, trazodone, ramelteon, tandospirone, etc.),
(8) others (varenicline, bupropion, atomoxetine, ibudilast, baclofen, buspirone, etc.), and the like.

EXAMPLE

Reference Example 1

1) Alcohol Withdrawal-Induced Locomotor Activity Increasing Action in Alcohol Dependence Mice In reference to a report that alcohol dependence can be formed by breeding mice on a liquid diet containing ethanol for 5 days (Narita M et al., Eur J Pharmacol 401 (2000) 191-5), and based on a report that rats bred on a liquid diet containing ethanol show increase in locomotor activity along with withdrawal syndrome after ethanol withdrawal (Iso H, Jpn J Psychopharmacol 3 (1983) 23-8), locomotor activity after withdrawal was measured in alcohol dependence mice. As a result, significant increase in locomotor activity was confirmed. The alcohol withdrawal-induced locomotor activity increasing action in the alcohol dependence mice may be deeply involved in various symptoms, particularly impulsive symptoms, associated with alcohol-related disorders.

The effect of combined use of brexpiprazole and nalmefene can be confirmed by measuring alcohol withdrawal-induced locomotor activity increasing action in alcohol dependence mice. Measurement method: Alcohol dependence mice are generated by breeding C57BL/6J mice (male) under individual housing for 5 days with free ingestion of skimmed milk containing 3% ethanol. On day 6, locomotor activity is measured after changing to an ethanol-free diet. An animal with average ethanol intake on days 2 to 4 of not less than 20 g/kg/day, and the body weight of not less than 14.5 g on day 5 is subjected to the test.

2) Preparation of Drug, Administration Method and Determination of Dose

Brexpiprazole is suspended in distilled water containing 5% gum arabic. The drug is orally administered to each mouse immediately before measurement of the locomotor activity on day 6. The dose of brexpiprazole is set to 0.02 to 0.03 mg/kg.

3) Preparation of Drug, Administration Method and Determination of Dose

Nalmefene hydrochloride monohydrate is dissolved in saline. The drug is subcutaneously administered to each mouse immediately before measurement of the locomotor activity on day 6. The dose of nalmefene hydrochloride monohydrate is set to 0.08 to 0.12 mg/kg.

4) Measurement of Locomotor Activity

The ethanol withdrawal-induced locomotor activity increasing action is measured by calculating difference between the locomotor activity on day 5 and the locomotor activity on day 6 after ethanol withdrawal in each animal.

Example 1

1) Measurement of Alcohol Intake by Limited Access Paradigm

Measurement method: An impulsive behavior of cravings for drinking alcohol was evaluated as follows by reference to the method of Sinclair et al. (Alcohol 1992; 9:441-44 and Alcohol & Alcoholism 2001; 36:2-10). First, Wistar rats (male) were allowed to freely drink 10% aqueous ethanol solution and tap water for several weeks under isolated rearing. After the ethanol intake of each animal became stable, limited access paradigm allowing ethanol intake only for 1 hr per day was started, and the ethanol intake in 1 hr was measured every day. The ethanol intake was calculated from the results of weight measurement of a water supply bottle filled with 10% aqueous ethanol solution immediately before the start of the limited access paradigm and immediately after the completion of the limited access paradigm. Animals that showed an average ethanol intake of not less than 0.4 g/kg/hr based on 100% ethanol in the limited access paradigm for 4 days immediately before drug evaluation were used. The limited access paradigm test was performed during 9:00 AM-4:00 PM.

2) Preparation of Drug, Administration Method and Determination of Dose

Brexpiprazole was suspended in distilled water containing 5% gum arabic. The drug was orally administered to each rat once per day for 4 days at 1 hr before the start of the limited access paradigm. The dose of brexpiprazole was selected to be 0.01 mg/kg that does not, by itself, influence the ethanol intake and the spontaneous locomotor activity under novel environments (data not shown).

3) Preparation of Drug, Administration Method and Determination of Dose

Nalmefene hydrochloride monohydrate (Tocris Bioscience) was dissolved in saline. The drug was subcutaneously administered to each rat once per day for 4 days at 1 hr before the start of the limited access paradigm. The dose of nalmefene hydrochloride monohydrate was selected to be 0.04 mg/kg that does not, by itself, influence the ethanol intake and the spontaneous locomotor activity under novel environments (data not shown).

4) Number of Rats

Twelve rats were used in total. A test using 3 rats per group was performed twice to make 6 rats for each group. The animals were repeatedly used after a sufficient period of drug cessation.

5) Statistical Analysis

The significance level of the test was set to 5%. As a statistical software, SAS (R9.3, SAS Institute Japan) was used. The difference between an average ethanol intake in the limited access paradigm for 4 days immediately before drug evaluation and an average ethanol intake in the limited access paradigm for 4 days during the drug administration period was calculated for every animal, and analyzed by two-way factorial analysis of variance by using the presence or absence of brexpiprazole and the presence or absence of nalmefene as factors.

6) Results

The test results are shown in FIG. 1.

To the rats confirmed to ingest ethanol at not less than 0.4 g/kg/hr on average of 4 days in the limited access paradigm were administered brexpiprazole orally at 0.01 mg/kg at 1 hr before ethanol intake and nalmefene hydrochloride monohydrate subcutaneously at 0.04 mg/kg at 20 min before ethanol intake, both for 4 days, and a difference between an average ethanol intake in the limited access paradigm for 4 days before administration and an average ethanol intake for 4 days during the dosing period was calculated and analyzed by two-way factorial analysis of variance. As a result, only the brexpiprazole and nalmefene combined use group showed a significant decrease in the ethanol intake (interaction: $p=0.0033$). This statistically shows that a combined use of the both drugs has a synergistic effect.

From the above-mentioned results, it has been clarified that, in the limited access paradigm to 10% aqueous ethanol solution, brexpiprazole and nalmefene can suppress impulsive ethanol intake behavior of Wistar rats by a combined use of extremely low doses thereof. There is a report stating that nalmefene, which has been clinically confirmed to suppress impulsive drinking behavior of patients with alcohol dependence and enable control of alcohol consumption, shows effects in this evaluation system when used singly at a dose about 10 times higher than the dose used in the present test (Alcohol & Alcoholism 2001; 36: 2-10). Therefore, the test results show that the combined use of the both medicaments not only suppresses impulsive drinking behavior of patients with alcohol dependence but also enables brexpiprazole to enhance treatment effects of nalmefene. Conversely, the test results show that the combined use of the both medicaments enables nalmefene to enhance treatment effects of brexpiprazole. Lower side effects are expected as a result of the lower doses that may be applied.

This application is based on patent application No. 2014-88148 filed in Japan, the entire contents of which are incorporated by reference herein.

The invention claimed is:

1. A method for reducing alcohol consumption in patients with alcohol dependence, comprising administering to a subject in need thereof:
   (a) brexpiprazole or a pharmaceutically acceptable salt thereof and nalmefene or a pharmaceutically acceptable salt thereof, wherein the brexpiprazole or a pharmaceutically acceptable salt thereof and the nalmefene or a pharmaceutically acceptable salt thereof are contained in a single preparation; or
   (b) a pharmaceutical composition containing brexpiprazole or a pharmaceutically acceptable salt thereof and a pharmaceutical composition containing nalmefene or a pharmaceutically acceptable salt thereof, wherein the pharmaceutical composition containing brexpiprazole or a pharmaceutically acceptable salt thereof and the pharmaceutical composition containing nalmefene or a pharmaceutically acceptable salt thereof are formulated for use in combination.

2. The method of claim 1, wherein the pharmaceutical composition containing brexpiprazole or a pharmaceutically acceptable salt thereof and the pharmaceutical composition containing nalmefene or a pharmaceutically acceptable salt thereof of (b) are administered simultaneously.

3. The method of claim 1, wherein the pharmaceutical composition containing brexpiprazole or a pharmaceutically acceptable salt thereof and the pharmaceutical composition containing nalmefene or a pharmaceutically acceptable salt thereof of (b) are administered in a staggered manner.

4. The method of any one of claims 1-3, wherein an existing therapeutic drug for alcohol-related disorder provides only an insufficient effect for the subject.

5. The method of claim 4, wherein the existing therapeutic drug for alcohol-related disorder is selected from the group consisting of cyanamide, disulfiram, acamprosate, nalmefene, and naltrexone.

* * * * *